United States Patent [19]

Bauer et al.

[11] Patent Number: 5,389,089
[45] Date of Patent: Feb. 14, 1995

[54] CATHETER WITH ANGLED BALL TIP FOR FALLOPIAN TUBE ACCESS AND METHOD

[75] Inventors: Otmar Bauer, Kludenbach, Germany; Steven R. Bacich, Laguna Niguel, Calif.

[73] Assignee: Imagyn Medical, Inc., Laguna Niguel, Calif.

[21] Appl. No.: 960,777

[22] Filed: Oct. 13, 1992

[51] Int. Cl.⁶ .............. A61M 5/00; A61M 31/00; A61M 29/00; A61B 17/43

[52] U.S. Cl. ...................... 604/271; 604/55; 604/906; 604/280; 600/35; 606/193

[58] Field of Search .............. 604/55, 96, 104, 264, 604/270, 271, 275, 279, 280, 281, 906; 600/33–35; 606/191–193, 195

[56] References Cited

U.S. PATENT DOCUMENTS

| | | | |
|---|---|---|---|
| 1,586,716 | 6/1926 | Snow | 604/275 |
| 1,861,769 | 6/1932 | Wappler. | |
| 2,024,982 | 12/1935 | Scott. | |
| 3,433,214 | 3/1969 | Silverman | 604/104 |
| 3,481,338 | 12/1969 | Sobel et al. | 604/264 |
| 3,605,750 | 9/1971 | Sheridan et al. | |
| 3,774,612 | 11/1973 | Marco | 604/275 |
| 3,978,863 | 9/1976 | Fettel et al. | |
| 4,013,079 | 3/1977 | Lindemann et al. | 606/191 |
| 4,136,695 | 1/1979 | Dafoe | 604/165 |
| 4,323,071 | 4/1982 | Simpson et al. | |
| 4,437,857 | 3/1984 | Goldstein et al. | 604/271 |
| 4,454,887 | 6/1984 | Kruger. | |
| 4,526,175 | 7/1985 | Chin et al. | 606/192 |
| 4,774,949 | 10/1988 | Fogarty. | |
| 4,990,138 | 2/1991 | Bacich et al. | 604/271 |
| 5,016,640 | 5/1991 | Ruiz | 604/281 |
| 5,147,315 | 9/1992 | Weber | 604/164 |

FOREIGN PATENT DOCUMENTS

| | | | |
|---|---|---|---|
| 2063553 | 12/1970 | Germany. | |
| 3115192 | 11/1981 | Germany. | |
| 542519 | 1/1977 | U.S.S.R. | 604/280 |

Primary Examiner—John D. Yasko
Assistant Examiner—Adam J. Cermak
Attorney, Agent, or Firm—Gordon L. Peterson

[57] ABSTRACT

A catheter for fallopian tube access comprising an elongated catheter body having a proximal region, a distal end and an elongated passage extending from the proximal region to the distal end. The elongated passage terminates in a distal opening at the distal end. The catheter body has an enlarged distal body portion and the distal opening is on the distal body portion. The distal body portion has a deflecting surface in the elongated passage adjacent the distal opening for directing a member or fluid passed through the elongated passage out of the distal opening along a path having a component which extends laterally of the catheter body.

23 Claims, 3 Drawing Sheets

CATHETER WITH ANGLED BALL TIP FOR FALLOPIAN TUBE ACCESS AND METHOD

BACKGROUND OF THE INVENTION

It is sometimes necessary or desirable to gain access to a fallopian tube for purposes of examination or carrying out a medical procedure. For example, the examination may be carried out with a flexible endoscope and the medical procedure may include depositing genetic material or infusing medication, dye or a contrast media into the fallopian tube.

A catheter can be used to gain access to a fallopian tube. To accomplish this, the catheter is inserted through the cervix into the uterus and then manipulated to place a distal opening of the catheter in registry with an ostium of the fallopian tube. A flexible instrument or fluid can then be passed through the catheter and into the fallopian tube.

One problem with gaining access to a fallopian tube is getting the distal opening of the catheter in proper registry with the ostium of the fallopian tube. The uterus in a normal, non-distended condition comprises two layers of tissue in closely adjacent confronting relationship, and the ostium or opening to the fallopian tube is relatively small. Consequently, it is difficult to work the catheter through the uterus to precisely the correct location and to move the confronting layers of tissue away from the ostium with the catheter. Once the catheter is properly positioned with the distal opening in registry with the ostium, it is sometimes difficult to pass a flexible member through the distal opening and cause it to properly enter the fallopian tube. This is the result of the angular relationship of the region of the fallopian tube near the ostium in relation to the uterus.

Another problem occurs as a result of the insertion of the catheter through the cervix. A conventional catheter with an on-axis distal opening acts like a scoop which picks up mucus and debris as the catheter is passed through the cervix. This can hinder visualization.

SUMMARY OF THE INVENTION

This invention provides a catheter and method which generally overcomes the problems identified above and which provides other advantages. With this invention, gaining access to a fallopian tube is facilitated and obtaining proper registry between the distal opening of the catheter and the ostium is made easier. In addition, the catheter and method of this invention can more accurately direct a member out of the catheter and into the fallopian tube. The distal opening of the catheter of this invention also collects less mucus and debris than the on-axis distal opening of the prior art.

The catheter of this invention preferably includes an elongated catheter body having a proximal region, a distal end and an elongated passage extending from the proximal region to the distal end. The elongated passage terminates in a distal opening at the distal end.

In order to push tissue away from the region closely adjacent the ostium, the catheter body has a distal body portion which is appropriately enlarged. For example, the distal body portion may have a larger radial dimension than a radial dimension of a region of the catheter body which is immediately proximal to the distal body portion. The elongated passage extends through the distal body portion. The distal opening and the distal end are on the distal body portion.

To increase the likelihood that the catheter can properly direct a member into the fallopian tube, the catheter has a deflecting surface in the elongated passage of the catheter body and adjacent the distal opening. The deflecting surface directs the member out of the distal opening along a path having a component which extends laterally of the catheter body. This path is more in alignment with the region of the fallopian tube adjacent the ostium than would be provided by a conventional catheter. Preferably the distal opening is radially offset from the axis of a major portion of the elongated passage proximally of the enlarged distal body portion, and the deflection surface is inclined radially to extend toward the distal opening.

To facilitate the pushing of tissue away from the ostium, the distal body portion preferably has an outer surface which is convexly curved as viewed in longitudinal cross section, and more preferably, the outer surface is curved in both axial and radial cross sections. In a preferred construction, the distal body portion is generally in the form of at least a portion of a ball.

In a preferred construction, the elongated passage of the catheter body has a major portion and a minor portion. The minor portion is in the distal body portion and extends laterally outwardly of the major portion. The minor portion is at least partially defined by the deflecting surface. The distal opening can advantageously face a direction which has a component extending laterally of the catheter body, or more specifically, the distal opening may lie in a plane which is inclined at an acute angle with respect to the axis of the major portion of the elongated passage. This offsetting of the distal opening provides a preferential orientation for leading into the fallopian tube at the desired angle. Moreover, by making the distal opening off-axis in this manner, it collects less mucus and debris as the catheter is being inserted through the cervix.

In order that the distal opening is inclined as desired, it is preferred that the distal end form an included angle with a reference plane of from about 15° to about 80°. A more preferred range is from about 50° to about 60°, and an angle of about 55° is considered optimum. The angular relationship is such that the deflecting surface deflects the member or fluid through an angle which is equal to or less than an included angle between the distal end and a radial reference plane.

Many features of this invention are adapted for both an everting catheter and a non-everting catheter. The everting catheter includes a support tube movable longitudinally within the elongated passage of the catheter body and a flexible everting element coupled to the catheter body and the support tube. The everting element is evertable out of the distal opening and is engageable with the deflecting surface so that the deflecting surface the deflects the everting element toward the distal opening during eversion.

In the case of a non-everting catheter, the member which is deflected by the deflecting surface may be a flexible endoscope or virtually any other elongated flexible instrument. In the case of an everting catheter, the member directly deflected by the everting surface is the everting element. However, any endoscope or instrument which is in or inserted or pulled through the everting element or any fluid passing through the everting element are also considered to be deflected by the deflecting surface.

To facilitate reaching an ostium, the catheter body preferably has a distal portion which is curved in one direction and a deflecting surface is arranged to deflect a member or fluid generally in a second direction which is away from the first direction. The catheter body is curved in this fashion in the normal or unstressed condition. The distal portion preferably forms an included angle of about 30° to about 165° with a more preferred range being from about 105° to about 135°. About 120° is considered optimum. The deflecting surface preferably deflects the member or fluid through an angle of from about 15° to about 85° with 25° to about 35° being more preferred. About 30° is considered optimum. These angles better adapt the catheter to reach an ostium.

With this invention, the length of the curved distal portion can be controlled to facilitate reaching an ostium. To accomplish this, the straight line distance from the proximal end of the distal portion at the axis of the catheter body to the distal end of the catheter body is preferably from about 1.5 cm to about 2.5 cm.

Another feature of this invention is to employ a scope lumen in the catheter body. The scope lumen is sized to receive an endoscope, and the scope lumen terminates adjacent the distal opening. An endoscope, which may be permanent or removable, may be provided in the scope lumen. The endoscope in the scope lumen is for observing a zone adjacent the distal opening and is primarily for the purpose of determining whether or not the member being passed into the fallopian tube has properly left the catheter and passed through the distal opening.

According to one method feature of this invention, a catheter is inserted through the cervix into the uterus and is then manipulated to place the distal opening in registry with an ostium of a fallopian tube. A flexible instrument or a fluid is then passed through the elongated passage to the deflecting surface and the deflecting surface deflects the instrument or fluid generally cranially through the distal opening and into the fallopian tube. When an everting catheter is used, a flexible instrument or fluid may passed through the support tube of the everting catheter to the everting element and then passed within the everting element and over the deflecting surface.

Another important method feature of this invention is to gain access to a fallopian tube of a patient utilizing an everting catheter which has the radially enlarged distal body portion. The enlarged distal body portion is used to push tissue away from the ostium, following which the everting element can be everted into the fallopian tube.

The invention, together with additional features and advantages thereof may best be understood by reference to the following description taken in connection with the accompanying illustrative drawings.

DESCRIPTION OF THE PREFERRED EMBODIMENT

Figure 1:
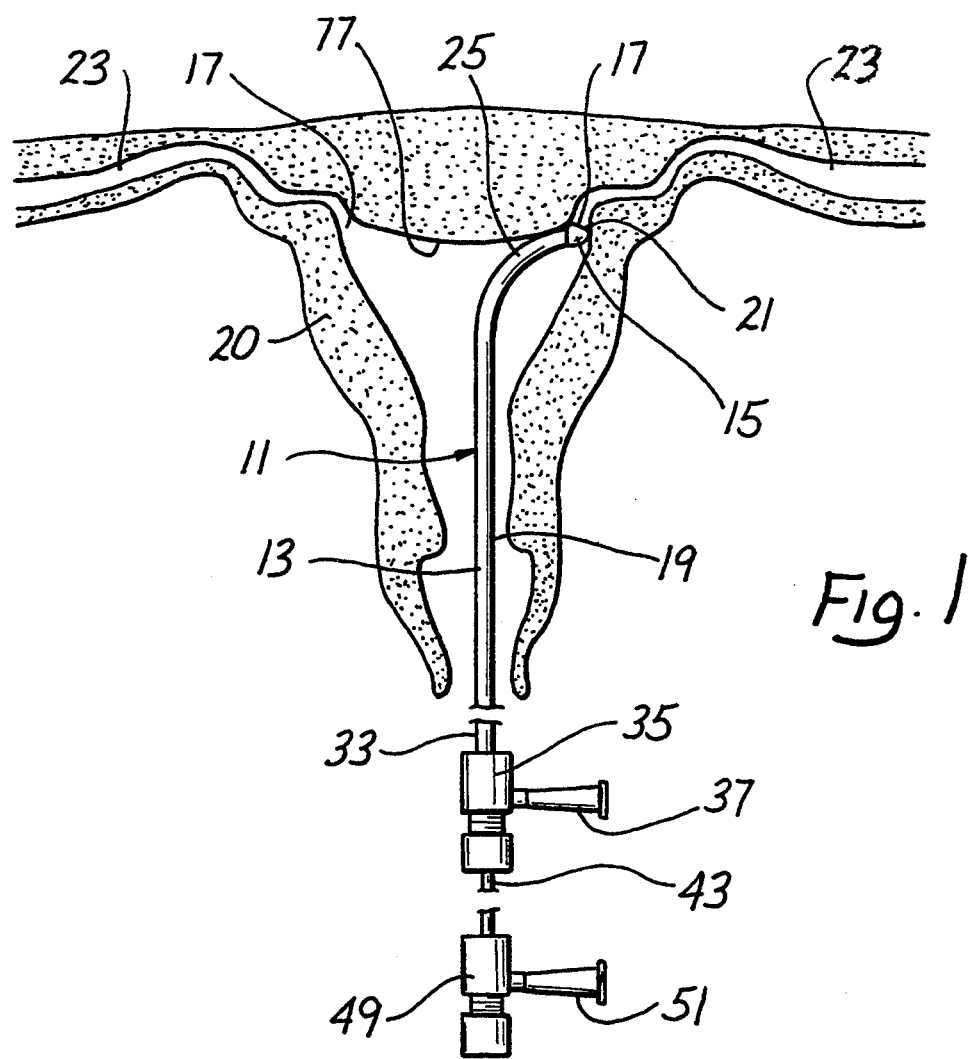
FIG. 1 is a fragmentary plan view illustrating one form of catheter of this invention within the body of a patient to achieve fallopian tube access.

FIG. 1 shows a catheter 11 which includes an elongated flexible catheter body 13 having an enlarged distal body portion 15 and a distal end 17. The catheter 11 has been passed through the cervix 19 and into the uterus 20 of a patient and has been manipulated to bring the distal end 17 to an ostium 21 of one of the fallopian tubes 23.

The catheter body 13 is flexible, but in its unstressed condition shown in FIG. 1, the catheter body 13 has a distal portion or region 25 which is curved in one direction. With reference to the patient, the curve opens generally laterally and inferiorly.

Figure 4:
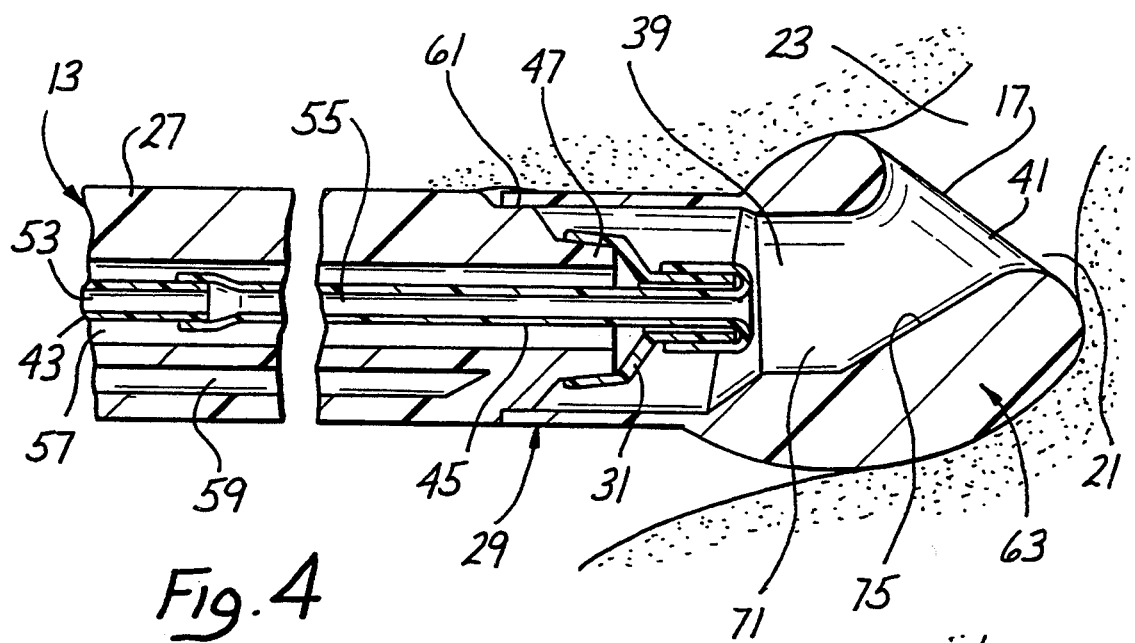
FIG. 4 is a fragmentary, longitudinal sectional view of the catheter in registry with an ostium of a fallopian tube and with the everting element inverted.

As shown in FIG. 4, the catheter body 13 includes a primary tube 27 which makes up most of the length of the catheter body, a distal segment 29 and an inner tubular member 31. The primary tube 27 is flexible and may be constructed of a suitable biocompatible polymeric material such as PTFE, nylon or polyethylene. The primary tube 27 is preferably reinforced by an outer tube (not shown) proximally of the distal portion 25. The primary tube 27 defines a proximal region 33 (FIG. 1) of the catheter body where it is coupled to a conventional fitting 35 which can be used to supply an inflation medium to the catheter through a leg 37.

The catheter body 13 has an elongated passage 39 which extends from the proximal region 33 and the fitting 37 to the distal end 17. The passage 39 terminates in a distal opening 41 (FIG. 4) at the distal end 17.

The catheter 11 is an everting catheter and includes a support tube 43 movable longitudinally within the elongated passage 39 and a flexible everting element 45 coupled to the support tube 43 and the catheter body 13 in any suitable manner such as by an adhesive or a thermal bond. More specifically, the everting element 45 is thermally bonded to the inner tubular member 31 which in turn is adhesively mounted on a reduced diameter nose section 47 of the primary tube 27 as shown in FIG. 4. The nose section 47 may be constructed of a biocompatible polymeric material, such as polyethylene. The support tube 43 extends from the location shown in FIG. 4 proximally completely through the elongated passage 39 and the fitting 35 and is coupled to a fitting 49 (FIG. 1). The fitting 49 includes a leg 51 through which a fluid can be infused through a central passage 53 of the support tube 43 and a passage 55 of the everting element 45. The fluid media for everting and inverting the everting element 45 can be injected through the leg 37 of the fitting 35 to an annular space 57 between the primary tube 27 and the support tube 43 as shown in FIG. 4.

The primary tube 27 has a blind mandrel lumen 59 into which a stiffening mandrel (not shown) can be inserted to straighten and stiffen the catheter 11 for insertion through the cervix into the uterus. The mandrel is then withdrawn to allow the catheter body 13 to return towards is curved unstressed state as shown in FIG. 1. This may all be accomplished as more specifically described in common assignee's copending application Ser. No. 779,356 filed on Oct. 17, 1991.

The distal segment 29 is preferably constructed of a suitable biocompatible polymeric material such as hard nylon, polyethylene or polyurethane. The distal segment 29 is bonded or otherwise attached to a reduced diameter portion 61 of the primary tube 27 so that the outer periphery of the catheter body 11 remains at substantially the same diameter on both sides of the transition between the primary tube 27 and the distal segment 29. The distal segment 29 forms a portion of the elongated passage 39 which extends through the catheter body 13.

Figure 2:
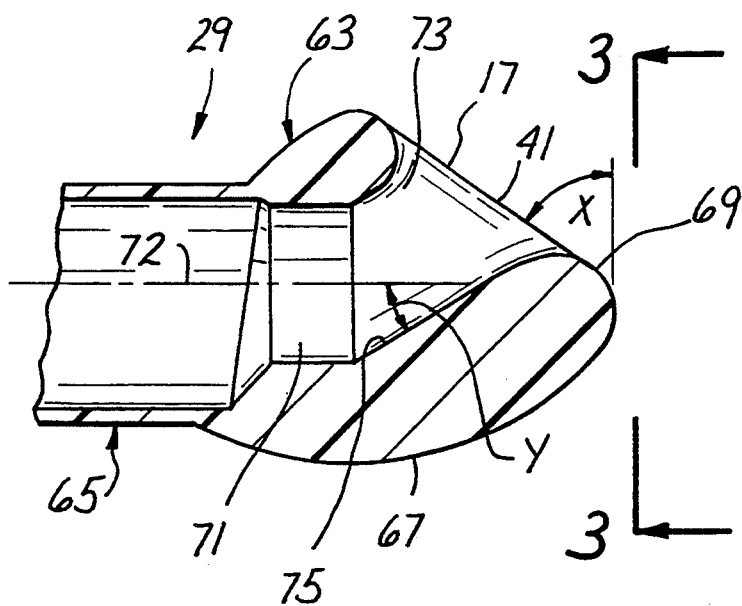
FIG. 2 is an enlarged fragmentary longitudinal sectional view of a distal segment of the catheter body.
Figure 3:
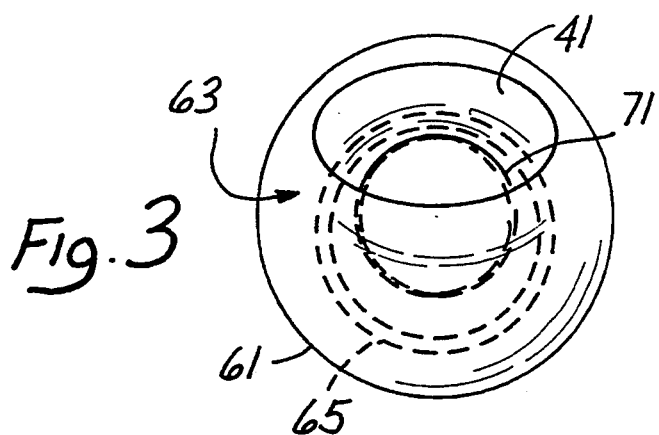
FIG. 3 is an end elevational view taken generally along line 3—3 of FIG. 2.

The distal segment 29 of the catheter body 13 includes an enlarged distal body portion 63 and a sleeve 65 (FIG. 2). The sleeve 65 is cylindrical to mate with the primary tube 27, which is also preferably cylindrical. The distal body portion 63 is enlarged, and in the embodiment illustrated, is generally in the form of a portion of a ball. Consequently, the distal body portion 63 has a larger radial dimension than a radial dimension of the region of the catheter body which is immediately proximal to the distal body portion, i.e. the sleeve 65. The distal body portion 63 has an outer surface 67 which is curved convexly in longitudinal cross section (FIG. 2) and as viewed in radial cross section. The distal body portion 63 is also harder and stiffer than the primary tube 27 and has an annular rounded surface 69 at the distal end 17 surrounding the distal opening 41 to facilitate insertion through the uterus to the ostium 21. The wall of the distal body portion 63 is thicker than the wall of the sleeve 65.

Internally, the distal body portion 63 has an axial cylindrical passage section 71 which is preferably coaxial with, or on a central axis 72 which is parallel to, the portion of the elongated passage 39 extending through the primary tube 27 and an inclined passage section 73 which extends from the passage section 71 to the distal opening 41. Thus, the elongated passage 39 through the catheter body 13 may be considered as having a major portion which extends from the fitting 35 all way through the axial passage section 71 and a minor portion, i.e. the inclined passage section 73, which extends laterally outwardly of the major portion as shown by way of example in FIG. 2.

The distal body portion 63 has a deflecting surface or ramp 75 which partially defines the inclined passage section 73 and which is inclined radially to extend toward the distal opening 41. The deflecting surface 75 can direct a member or fluid out of the distal opening along a path having a component which extends laterally of the catheter body 13.

With this construction, the distal opening 41 faces in a direction which has a component extending laterally of the catheter body 13. The distal opening 41 is radially offset from the axis of the major portion of the elongated passage 39 proximally of the enlarged distal body portion, i.e. the distal opening 41 is radially offset from the axis of the cylindrical passage section 71 as well as the portions of the passage 39 proximally of the axial passage section 71. The distal opening 41 also lies in a plane which is inclined at an acute angle with respect to the axis of the major portion of the elongated passage 39 and is off axis with respect to the major portion of the elongated passage.

The distal opening 41 is preferably substantially circular and the inclined passage section 73 may be substantially cylindrical. Thus, the deflecting surface 75 represents only a portion of the cylindrical surface defining the inclined passage section 73.

Although various constructions are possible, in this embodiment the deflecting surface 75 forms an angle Y of about 30° with the central axis 72 of the axial passage section 71. The plane of the distal end 17 and of the distal opening 41 forms an angle X with a vertical or radial reference plane which is optimally about 55°. In this embodiment the angle Y is less than the angle X.

Figure 5:
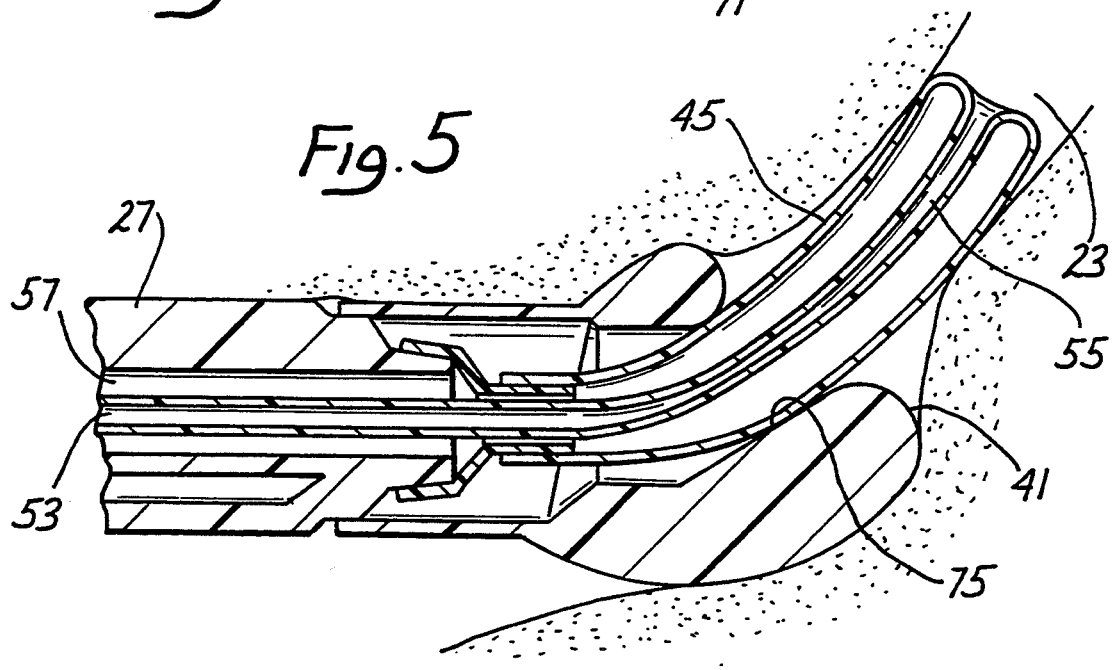
FIG. 5 is a sectional view similar to FIG. 4 with the everting element everted.

By comparing FIG. 1 with FIGS. 2, 4 and 5, it can be seen that the distal portion 25 is curved in one direction, and the deflecting surface is constructed and arranged to direct the member or fluid being passed through the elongated passage out of the distal opening 41 in a second direction which is away from the first direction. Specifically, the deflecting surface 75 directs a member or fluid generally superiorly or cranially. Thus, a member or fluid passing through the elongated passage 39 is subjected to compound motion from the distal portion 25 and the deflecting surface 75. As viewed for example in FIGS. 1 and 2, the distal portion 25 curves to the right and the deflecting surface 75 causes a change of direction to the left. Although various constructions are possible, in this embodiment the distal portion 25 in its unstressed condition extends through or forms an included angle of about 120°. As shown in FIG. 1, this included angle is less than 120°. This is the result of the catheter 11 being deflected by virtue of its engagement with the fundus or end wall 77 of the uterus 20.

Figure 1A:
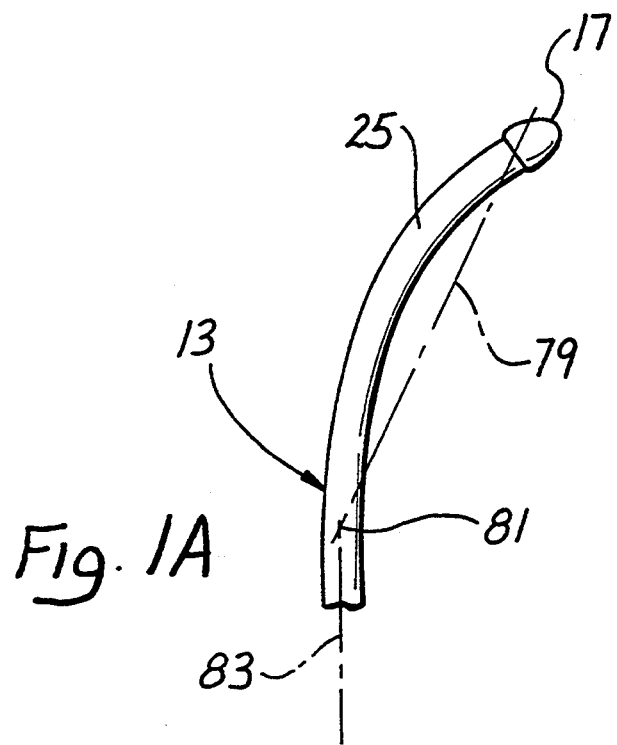
FIG. 1A is a fragmentary plan view of a portion of the catheter in an unstressed condition.

FIG. 1A shows the catheter 11 out of the patient with the distal portion 25 in the unstressed condition. Thus, FIG. 1A shows the distal portion 25 forming an included angle of about 120°. As shown in FIG. 1A, the straight line distance as measured along a straight reference line 79 from a proximal end 81 of the distal portion 25 at the axis 83 of the catheter body 13 to the distal end 17 is about 2 cm. As shown in FIG. 1A, the straight line 79 terminates centrally in the distal end 17, and in this embodiment, it terminates at the center of the distal opening 41 (FIG. 2).

In use, the catheter 11 with the mandrel (not shown) in the mandrel lumen 59 is inserted through the cervix 19 into the uterus 20 whereupon the mandrel is withdrawn and the catheter 11 is allowed to assume its essentially unstressed condition in which the distal portion 25 is curved as shown by way of example in FIG. 1. Because the distal opening 41 lies in an off-axis position during insertion, it collects a reduced quantity of mucus during the insertion process. The catheter 11 is then manipulated to place the distal opening 41 in registry with the ostium 21 of the fallopian tube 23. The enlarged distal body portion 63 separates the tissues adjacent the ostium 21. Next, an everting fluid is applied through the leg 37 of the fitting 35 to the annular space 57 to evert the everting element 45 as shown for example in. FIG. 5. The deflecting surface 75 deflects the everting element 45 towards the distal opening 41 as the everting element is being everted. The deflection of the everting element 45 is generally cranially and into the fallopian tube 23. In this position, an instrument or fluid can be passed through the central passage 53 into the fallopian tube for examination, treatment or other medical purposes. Whatever is passed through the central passage 53 is also deflected by the deflecting surface 75 in that the deflecting surface 75 brings about or has brought about the deflection of the everting element 45. Of course, the everting element 45 may pull an instrument into the fallopian tube 23 as it is being everted, if desired. Upon completion of the examination or procedure, the everting element 45 can be inverted back to the position of FIG. 4 by reducing the pressure of the everting medium in the annular space 55 and withdrawing the fitting 49 and the support tube 43 proximally in accordance with conventional practice.

Figure 6:
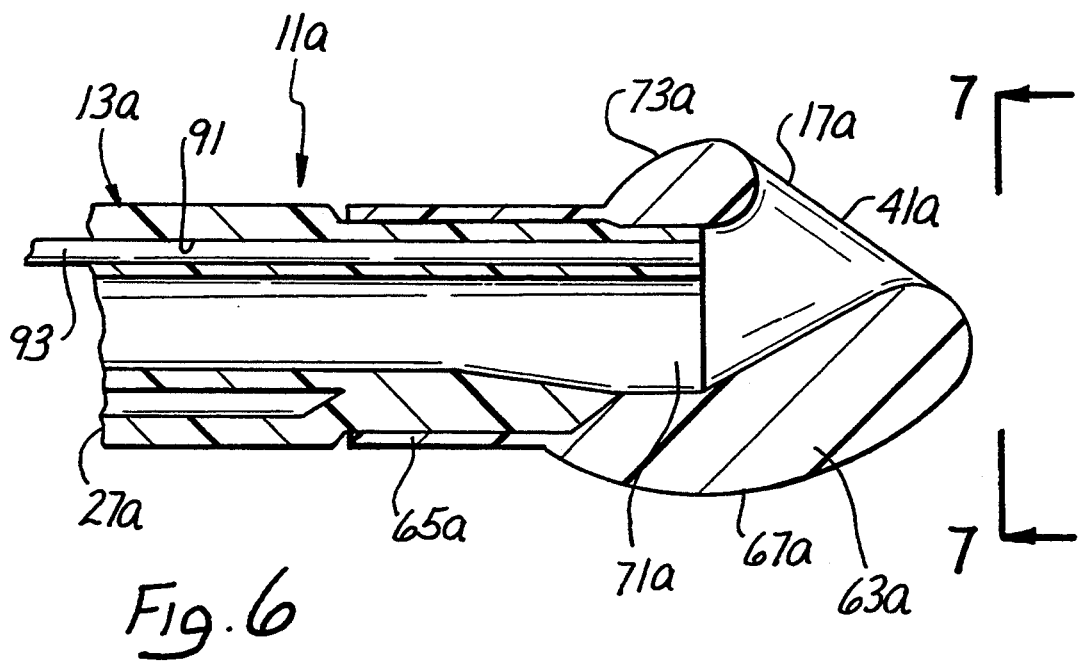
FIG. 6 is a longitudinal sectional view similar to FIG. 4 of a second embodiment of catheter constructed in accordance with the teachings of this invention.
Figure 7:
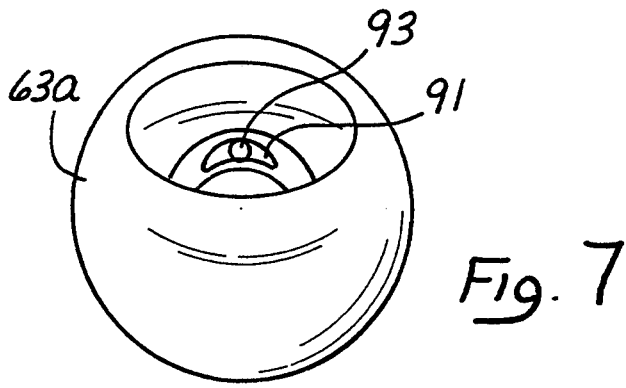
FIG. 7 is an end elevational view taken generally along line 7—7 of FIG. 6.

FIGS. 6 and 7 show a catheter 11a which is identical to the catheter 11 in all respects not shown or described herein. Portions of the catheter 11a corresponding to portions of the catheter 11 are designated by corresponding reference numerals followed by the letter a.

The primary difference between the catheters 11a and 11 is that the latter is a non-everting catheter and has a scope lumen 91 with an endoscope 93 in the lumen 91. The endoscope 93 may be either removable from the scope lumen 91 or permanently affixed within the lumen 91. The scope lumen 91 terminates distally at the juncture of the passage sections 71a and 73a and the scope 93 preferably extends to the distal end of the scope lumen 91. In this position, the scope 93 can be used to observe whether or not the distal opening 41a is in proper registry with the ostium 17 (FIG. 4) as well as observe any member or fluid being supplied by the catheter 11a to the fallopian tube.

Because the catheter 11a is of the non-everting type, the everting element 45 and the nose section 47 of the embodiment of FIGS. 1–5 are eliminated and the primary tube 27 extends completely through the sleeve 65a of the distal body portion 63a. The scope lumen 91 is provided in the primary tube 27a, and the primary tube 27a extends to the distal end of the axial cylindrical passage section 71a.

Although exemplary embodiments of the invention have been shown and described, many changes, modifications and substitutions may be made by one having ordinary skill in the art without necessarily departing from the spirit and scope of this invention.

We claim:

1. A catheter for fallopian tube access comprising:
   an elongated catheter body having a proximal region, a distal end and an elongated passage extending from the proximal region to the distal end, said passage terminating in a distal opening at the distal end;
   said catheter body having a distal body portion which has a larger radial dimension than a radial dimension of a region of the catheter body which is immediately proximal to said distal body portion, said elongated passage extending through the distal body portion, the distal opening and said distal end being on said distal body portion;
   said distal body portion having a deflecting surface in said elongated passage adjacent the distal opening for directing a member or fluid out of the distal opening along a path having a component which extends laterally of the catheter body; and
   a support tube movable longitudinally within the elongated passage and a flexible everting element coupled to the catheter body and the support tube, said everting element being deflectable by the deflecting surface toward the distal opening and evertable out of the distal opening.

2. A catheter as defined in claim 1 wherein the distal body portion has an outer surface which is convexly curved as viewed in longitudinal cross section.

3. A catheter as defined in claim 2 wherein said elongated passage has a major portion and a minor portion, the minor portion is in the distal body portion and extends laterally outwardly of the major portion and is at least partly defined by the deflecting surface.

4. A catheter as defined in claim 3 wherein the deflecting surface can deflect the member or fluid through an angle from about 25° to about 35°.

5. A catheter as defined in claim 1 wherein the distal body portion has an outer surface which is curved in both axial and radial cross sections.

6. A catheter as defined in claim 1 wherein the distal opening faces a direction which has a component extending laterally of the catheter body.

7. A catheter as defined in claim 1 wherein the deflecting surface deflects the everting element through an angle of about 15° to about 85°.

8. A catheter as defined in claim 1 wherein the catheter body has a distal portion which is curved in a first direction and the deflecting surface is arranged to deflect the everting element generally in a second direction which is away from the first direction.

9. A catheter as defined in claim 1 wherein the distal end forms an included angle with a radial reference plane of from about 15° to about 80°.

10. A catheter as defined in claim 1 wherein the distal end forms an included angle with a radial reference plane of from about 50° to about 60°.

11. A catheter as defined in claim 1 wherein the deflecting surface deflects the everting element through an angle which is equal to or less than an included angle between the distal end and a radial reference plane.

12. A catheter for fallopian tube access comprising:
    an elongated catheter body having a distal portion which in an unstressed condition is curved in a first direction;
    said catheter body having a proximal region, a distal end and an elongated passage extending from the proximal region to the distal end, said passage terminating in a distal opening which opens at the distal end; and
    said catheter body having a deflecting surface in said elongated passage adjacent the distal opening for directing a member or fluid being passed through said elongated passage out of the distal opening in a second direction which is away from the first direction such that the catheter can direct the member or fluid into a fallopian tube.

13. A catheter as defined in claim 12 including a scope lumen in said catheter body sized to receive an endoscope and terminating adjacent the distal opening.

14. A catheter as defined in claim 13 including an endoscope in said scope lumen for observing a zone adjacent the distal opening.

15. A catheter as defined in claim 12 wherein the distal portion forms an included angle of from about 105° to about 135°.

16. A catheter as defined in claim 12 wherein the deflecting surface can deflect the member or fluid through an angle of from about 25° to about 35°.

17. A catheter as defined in claim 12 wherein the straight line distance from the proximal end of the distal portion at the axis of the catheter body to said distal end is from about 1.5 cm to about 2.5 cm.

18. A catheter as defined in claim 12 including a support tube movable longitudinally within the elongated passage and a flexible everting element coupled to the catheter body and the support tube, said everting element being engageable with the deflecting surface and evertable out of the distal opening.

19. A catheter as defined in claim 12 wherein the distal opening opens at the distal end prior to using the catheter for fallopian tube access.

20. A catheter for fallopian tube access comprising:
an elongated catheter body having a proximal region, a distal end and an elongated passage extending from the proximal region to the distal end, said passage terminating in a distal opening at the distal end;
said catheter body having a distal body portion which has a larger radial dimension than a radial dimension of a region of the catheter body which is immediately proximal to said distal body portion, said elongated passage extending through the distal body portion, the distal opening and said distal end being on said distal body portion;
said elongated passage having a major portion and a minor portion, the minor portion being in the distal body portion and extending laterally outwardly of the major portion; and
said distal body portion having a deflecting surface in said elongated passage adjacent the distal opening for deflecting a member or fluid through an angle from about 25° to about 35° out of the distal opening along a path having a component which extends laterally of the catheter body whereby the catheter can direct the member or fluid into a fallopian tube, said deflecting surface at least partially defining said minor portion of said elongated passage.

21. A catheter for fallopian tube access comprising:
an elongated catheter body having a proximal region, a distal end and an elongated passage extending from the proximal region to the distal end, said passage terminating in a distal opening which opens at the distal end;
said catheter body having a distal body portion which has a larger radial dimension than a radial dimension of a region of the catheter body which is immediately proximal to said distal body portion, said elongated passage extending through the distal body portion, the distal opening and said distal end being on said distal body portion;
said distal body portion having a deflecting surface in said elongated passage adjacent the distal opening for directing a member or fluid out of the distal opening along a path having a component which extends laterally of the catheter body; and
the catheter body having a distal portion which is curved in a first direction and the deflecting surface being arranged to deflect a member or fluid generally in a second direction which is away from the first direction such that transcervical access to an ostium of a fallopian tube is facilitated and the catheter can direct a member or fluid into the fallopian tube.

22. A catheter as defined in claim 21 wherein the distal portion forms an included angle of from about 30° to about 165°.

23. A catheter for fallopian tube access comprising:
a flexible, elongated catheter body having a proximal region, a distal end and an elongated passage extending from the proximal region to the distal end, said passage terminating in a distal opening at the distal end;
said catheter body having an enlarged distal body portion which has an outer surface which is convexly curved as viewed in axial and radial cross section, said elongated passage extending through the distal body portion and having a major portion and a minor inclined passage section, said major portion terminating in the inclined passage section and the inclined passage section extending from said major portion to said distal opening, the distal opening and said distal end being on said distal body portion;
said distal opening being radially offset from the axis of said major portion of the elongated passage proximally of the enlarged distal body portion;
said inclined passage section having a deflecting surface adjacent the distal opening, whereby the deflecting surface can deflect a member or fluid through an acute angle toward the distal opening;
the distal opening lying in a surface region of the distal body portion which is inclined at an acute angle X with respect to a reference plane perpendicular to the axis of said major portion of the elongated passage;
said surface region and said distal opening extending proximally and radially outwardly as they extend away from the deflecting surface;
the deflecting surface deflecting the member or fluid through an angle which is equal to or less than the angle X; and
said distal opening at the distal end.

* * * * *